US006403819B1

(12) United States Patent
Bright et al.

(10) Patent No.: US 6,403,819 B1
(45) Date of Patent: Jun. 11, 2002

(54) PROCESS FOR MAKING DI(HYDROXYALKYLARYL) ARYL PHOSPHATE COMPOUNDS

(75) Inventors: Danielle A. Bright, New City; Jeffrey E. Telschow, Tarrytown, both of NY (US)

(73) Assignee: Akzo Nobel, NV, Arnhem (NL)

( * ) Notice: Subject to any disclaimer, the term of this patent is extended or adjusted under 35 U.S.C. 154(b) by 0 days.

(21) Appl. No.: 08/859,856

(22) Filed: May 21, 1997

(51) Int. Cl.⁷ .................................................. C07F 9/12
(52) U.S. Cl. ......................... 558/99; 558/100; 558/194
(58) Field of Search ........................... 558/194, 99, 100

(56) References Cited

U.S. PATENT DOCUMENTS

| | | | |
|---|---|---|---|
| 3,076,011 A | 1/1963 | Hamermesh et al. | 260/461 |
| 5,278,212 A | 1/1994 | Nishihara et al. | 524/141 |

FOREIGN PATENT DOCUMENTS

| | | | |
|---|---|---|---|
| JP | 223158/1989 | 9/1989 | C08L/71/04 |

OTHER PUBLICATIONS

STN International, Registry Database, Registry No. 1330–78–5, accessed Jan. 15, 2002.*
Grant and Hackh's Chemical Dictionary, Fifth Edition, McGraw–Hill, Inc., New York, 1987, p. 158.*
English translation of JP 03–138195 (Ricoh Co., Ltd.), originally published in Japanese on Jul. 9, 1992.*
English translation of JP 04–191092 (Ricoh Co. Ltd.), originally published in Japanese on Jun. 12, 1991.*
Database CAPLUS on STN®, Chemical Abstracts Service, (Columbus, Ohio), Accession No. 1992:117282, JP 03–138195, abstract.*
Database CAPLUS on STN®, Chemical Abstracts Service, (Columbus, Ohio), Accession No. 1993:30111, JP 04–191092, abstract.*
Chemical Abstracts, vol. 120, 9796t (1994).

\* cited by examiner

*Primary Examiner*—Michael G. Ambrose
(74) *Attorney, Agent, or Firm*—Richard P. Fennelly

(57) ABSTRACT

A process for the formation of a di(hydroxyalkylaryl) aryl phosphate is disclosed which comprises the reaction of an o-alkyl substituted aromatic diol, e.g., an o-alkyl substituted hydroquinone such as o-t-butylhydro-quinone, and monoaryl dihalophosphate, such as monophenyl dichlorophosphate. This process can, in particular, be used to make certain di(hydroxy-o-alkylphenyl) phenyl phosphate compounds, preferably those that are p-hydroxy, such as di(p-hydroxy-o-t-butylphenyl) phenyl phosphate.

6 Claims, No Drawings

PROCESS FOR MAKING DI(HYDROXYALKYLARYL) ARYL PHOSPHATE COMPOUNDS

BACKGROUND OF THE INVENTION

U.S. Patent No. 3,076,011 to C. L. Hamermesh et al. discloses a variety of phosphorus-containing monomers of the general formula $(H\text{—}A\text{—}O)_2\text{—}P(O)\text{—}R$, where A can be $\text{—}OC_6H_4\text{—}$ and R can be $C_6H_5O$.

Japanese Patent Publication No. 290,086/1993 describes the use, as flame retardants for thermoplastic resins, of monophosphate compounds of the formula $(R^1O)_nP(O)(OR^2OH)_{3-n}$, where n can be 0 to 2, $R^1$ can be lower alkyl, and $R^2$ can be arylene, or diarylene. These flame retardant compounds are prepared from phenol, resorcinol, and phosphorus oxytrichloride as reagents.

U.S. Pat. No. 5,278,212 to H. Nishihara et al. describes the use of certain hydroxyphenyl-containing organophosphorus compounds as flow modifiers for thermoplastic resins. Formula (I) for such compounds contemplates certain "R" groups on the various phenyl rings shown therein where those "R" groups are taught as each representing certain groups including hydroxyl, hydrogen "or" an alkyl group of from one to six carbon atoms. This reference, for example, illustrates a dihydroxyphenyl phenyl phosphate compound (which is designated "TPP-(OH)$_2$"), which is free of alkyl substitution on all three of its phenyl rings, at Col. 14, lines 60–65.

The process used to synthesize the product desired by the patentees of Japanese Patent Publication No. 223,158/1989 relies, for example, upon the reaction of a mixture of phenol and aromatic diol (e.g., resorcinol) with phosphorus oxychloride in the presence of a catalyst (e.g., aluminum chloride).

SUMMARY OF THE INVENTION

The present invention relates to a process for the formation of a di(hydroxyalkylaryl) aryl phosphate which comprises the reaction of an o-alkyl substituted aromatic diol, e.g., an o-alkyl substituted hydroquinone such as o-t-butylhydroquinone, and monoaryl dihalophosphate, such as monophenyl dichlorophosphate. The di(hydroxyalkylaryl) aryl phosphate compositions of this invention are useful as flame retardant additives for thermoplastic and thermoset resins.

The present invention also relates to certain di(hydroxy-o-alkylaryl) aryl phosphate compounds, preferably those that are p-hydroxy, such as di(p-hydroxy-o-t-butylphenyl) phenyl phosphate.

DESCRIPTION OF PREFERRED EMBODIMENTS

As previously described, the invention relates to a process for the formation of a di(hydroxyalkylaryl) arylphosphate which comprises the reaction of an o-alkyl substituted aromatic diol and a monoaryl dihalophosphate.

The o-alkyl substituted aromatic diol contains an alkyl substituent which can be either straight or branched chain of from one to about six carbon atoms in size. Branched structures of from three to six carbon atoms are preferred as exemplified by t-butyl. The hydroxy groups are preferably para- to one another as in hydroquinone. An especially preferred reagent for use is o-t-butylhydroquinone.

The monoaryl dihalophosphate is of the formula $ArOP(O)X_2$, where Ar stands for substituted or unsubstituted aryl, and X stands for halo, such as chloro or bromo. The preferred aryl group is phenyl. A particularly preferred reagent to use is monophenyl dichlorophosphate.

The reaction for forming the desired compounds, which will be described in greater detail below, is between one mole of monoaryl dihalophosphate and two moles of the o-alkyl substituted aromatic diol. This reaction is preferably conducted at an elevated temperature of about 50° C. to about 200° C. using an effective amount (about 0.1% to about 0.5%, by weight of the diarylhalophosphate) of a Lewis acid catalyst, such as magnesium dichloride.

The reaction of the present invention also forms certain di(hydroxy-o-alkylphenyl) phenyl phosphate compounds which are believed to be novel. These compounds can be illustrated, in a preferred embodiment, by the following general formula:

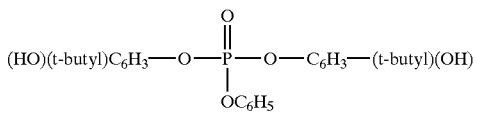

wherein, in a most preferred embodiment, both hydroxy substituents are in the para position and both t-butyl substituents, as the chosen alkyl substituents, are in the ortho position.

The resulting di(hydroxyalkylaryl) arylphosphate product can be used as a reactive type flame retardant for polymer matrices, such as epoxy and polyurethane, and as an additive or reactive-type flame retardant in thermoplastic resins, for example, in polycarbonate resin compositions, including those of the type described in U.S. Pat. No. 5,618,867. It can be incorporated, for example, in the resin backbone.

The present invention is further illustrated by the Examples which follow.

EXAMPLE 1

Phenyldichlorophosphate (50.0 g, 0.237 mole), t-butylhydroquinone (78.8 g, 0.474 mole), magnesium dichloride (0.3 g) and 200 ml of toluene were added to a 500 ml four-necked flask equipped with a mechanical stirrer, thermometer, reflux condenser, and nitrogen inlet and outlet. The mixture was brought to reflux (about 110° C.), and reflux was maintained for eight hours.

After that period of time had elapsed, a sample from the reactor was analyzed by liquid chromatography. Excluding the solvent, the main product (about 80%) was the desired di(t-butylhydroquinyl)phenyl phosphate. Other impurities included 4.1% by weight of unreacted t-butylhydroquinone and the same amount of di(t-butyl hydroquinone).

Upon evaporation of toluene and addition of methanol, a white solid which melted at 159° C. to 164° C. was isolated. Analysis of the product by $^{13}C$ and $^{31}P$ NMR gave the following composition: 92.5 wt % of di(t-butylhydroquinyl) phenyl phosphate; 4.8 wt % of t-butylhydroquinyl diphenyl phosphate and 2.7 wt % of triphenyl phosphate.

EXAMPLE 2

The product from Example 1 was evaluated for its effectiveness as a flame retardant in epoxy resin (EPON 828 brand) by the Limiting Oxygen Index (LOI) method. The ratio of epoxy resin to flame retardant was adjusted to produce a 2 wt % phosphorus level in the composite. The epoxy/flame retardant composite was cured using 2-ethyl- 4-methyl imidazole as the curing agent. The following results were obtained:

| Epoxy/FR Ratio (Wt. Basis) | % P | LOI |
|---|---|---|
| 100/0 (Control) | 0.0 | 18.5 |
| 70/30 | 2.0 | 26.5 |

EXAMPLE 3

The product from Example 1 was evaluated for its effectiveness as a flame retardant in a high impact polystyrene (HIPS) blend containing polyphenylene ether (PPE) by the LOI method. Blend specimens were prepared by solution casting from chloroform. The following results were obtained:

| HIPS/PPE/FR Ratio (Wt. Basis) | % P | LOI |
|---|---|---|
| 100/0/0 (Control) | 0.0 | 17 |
| 80/20/0 (Control) | 0.0 | 19 |
| 80/20/20 | 1.1 | 22.5 |

EXAMPLE 4

The product from Example 1 was evaluated for its effectiveness as a flame retardant in a HIPS/PPE blend by the UL-94 method on a ⅛ inch specimen. Melamine cyanurate (MC) was employed as a co-additive in one run. The following results were obtained:

| HIPS/PPO/FR/MC Ratio (Wt. Basis) | % P | UL-94 |
|---|---|---|
| 80/20/0/0 | 0 | Fail |
| 80/20/20/8 | 1.04 | V-1 |

The foregoing Examples, since they are intended to merely illustrate certain embodiments of the present invention, should not be construed in a limiting sense. The scope of protection sought is set forth in the claims which follow.

We claim:

1. A process for the formation of a di(hydroxyalkylphenyl) aryl phosphate which comprises the reaction of an o-alkyl) substituted aromatic diol and a monoaryl dihalophosphate.

2. A process as claimed in claim 1 wherein the o-alkyl substituted aromatic diol is an o-alkyl substituted hydroquinone.

3. A process as claimed in claim 2 wherein the o-alkyl substituted aromatic diol is an o-t-butylhydroquinone.

4. A process as claimed in claim 1 wherein the monoaryl dihalophosphate is monophenyl dichlorophosphate.

5. A process as claimed in claim 1 wherein the monoaryl dihalophosphate is monophenyl dichlorophosphate and the o-alkyl substituted aromatic diol is an o-alkyl substituted hydroquinone.

6. A process as claimed in claim 1 wherein the monophenyl dihalophosphate is monophenyl dichlorophosphate and the o-alkyl substituted aromatic diol is o-t-butylhydroquinone.

* * * * *